(12) United States Patent
Ducote, Jr. et al.

(10) Patent No.: US 11,629,912 B2
(45) Date of Patent: Apr. 18, 2023

(54) DEHYDROGENATION SEPARATION UNIT WITH MIXED REFRIGERANT COOLING

(71) Applicant: Chart Energy & Chemicals, Inc., Ball Ground, GA (US)

(72) Inventors: Douglas A. Ducote, Jr., The Woodlands, TX (US); Brent A. Heyrman, The Woodlands, TX (US); Timothy P. Gushanas, Pearland, TX (US); Richard Hopewell, Medfield, MA (US)

(73) Assignee: Chart Energy & Chemicals, Inc., Ball Ground, GA (US)

( * ) Notice: Subject to any disclaimer, the term of this patent is extended or adjusted under 35 U.S.C. 154(b) by 0 days.

(21) Appl. No.: 17/715,711

(22) Filed: Apr. 7, 2022

(65) Prior Publication Data

US 2022/0228802 A1     Jul. 21, 2022

Related U.S. Application Data

(63) Continuation of application No. 17/104,307, filed on Nov. 25, 2020, which is a continuation-in-part of (Continued)

(51) Int. Cl.
*F25J 3/02*     (2006.01)
*F25J 1/00*     (2006.01)
*F25J 1/02*     (2006.01)

(52) U.S. Cl.
CPC .......... *F25J 1/0022* (2013.01); *F25J 1/0055* (2013.01); *F25J 1/0292* (2013.01);
(Continued)

(58) Field of Classification Search
CPC .... F25J 3/06; F25J 3/065; F25J 3/0645; F25J 3/0655; F25J 3/0209; F25J 3/0214;
(Continued)

(56) References Cited

U.S. PATENT DOCUMENTS 3,626,705 A * 12/1971 Knapp et al. ............ F25J 3/062
                                                          62/3.1
4,217,759 A      8/1980 Shenoy
(Continued)

FOREIGN PATENT DOCUMENTS

CN        1509262 A      6/2004
CN     203187601 U       9/2013
(Continued)

OTHER PUBLICATIONS

Chinese Search Report for Chinese Application No. 20198006672098 dated Aug. 9, 2022.
(Continued)

*Primary Examiner* — Brian M King
(74) *Attorney, Agent, or Firm* — Cook Alex Ltd.

(57) ABSTRACT

A main heat exchanger receives and partially condenses an effluent fluid stream so that a mixed phase effluent stream is formed. A primary separation device receives and separates the mixed phase effluent stream into a primary vapor stream including hydrogen and a primary liquid stream including an olefinic hydrocarbon. The main heat exchanger receives and warms at least a portion of the primary vapor stream to provide refrigeration for partially condensing the effluent fluid stream. The main heat exchanger also receives, warms and partially vaporizes the primary liquid stream. A mixed refrigerant compression system also provides refrigeration in the main heat exchanger.

20 Claims, 11 Drawing Sheets

Related U.S. Application Data application No. 16/595,866, filed on Oct. 8, 2019, now Pat. No. 11,543,181.

(60) Provisional application No. 62/743,263, filed on Oct. 9, 2018.

(52) U.S. Cl.
CPC ........ *F25J 2220/62* (2013.01); *F25J 2220/64* (2013.01); *F25J 2270/66* (2013.01)

(58) Field of Classification Search
CPC .... F25J 3/0252; F25J 2205/40; F25J 2205/82; F25J 2210/06; F25J 2220/42
See application file for complete search history.

(56) References Cited

U.S. PATENT DOCUMENTS

| | | | |
|---|---|---|---|
| 4,707,170 A | 11/1987 | Ayres et al. | |
| 4,921,514 A | 5/1990 | Rowles et al. | |
| 5,329,774 A | 7/1994 | Tanguay et al. | |
| 5,626,034 A | 5/1997 | Manley et al. | |
| 5,657,643 A | 8/1997 | Price | |
| 5,746,066 A | 5/1998 | Manley | |
| 6,333,445 B1 * | 12/2001 | O'Brien | F25J 3/0655 585/800 |
| 6,560,989 B1 | 5/2003 | Roberts et al. | |
| 6,581,409 B2 | 6/2003 | Wilding et al. | |
| 6,637,237 B1 | 10/2003 | Wei et al. | |
| 6,705,113 B2 | 3/2004 | Wei et al. | |
| 7,065,974 B2 | 6/2006 | Grenfell | |
| 7,082,787 B2 | 8/2006 | Lee et al. | |
| 7,278,264 B2 | 10/2007 | Brostow | |
| 7,437,891 B2 | 10/2008 | Reyneke et al. | |
| 8,013,201 B2 | 9/2011 | Panditrao | |
| 8,563,793 B2 | 10/2013 | Zimmermann et al. | |
| 9,574,822 B2 | 2/2017 | Haberberger et al. | |
| 9,746,234 B2 | 8/2017 | Byfield et al. | |
| 2002/0174679 A1 | 11/2002 | Wei | |
| 2006/0149115 A1 | 7/2006 | Foral et al. | |
| 2007/0208432 A1 | 9/2007 | Hawrysz | |
| 2010/0186929 A1 | 7/2010 | Chantant et al. | |
| 2010/0217059 A1 | 8/2010 | Reyneke et al. | |
| 2010/0281915 A1 | 11/2010 | Roberts et al. | |
| 2011/0146342 A1 | 6/2011 | Sumner | |
| 2011/0226008 A1 | 9/2011 | Gushanas et al. | |
| 2014/0260415 A1 | 9/2014 | Ducote, Jr. et al. | |
| 2015/0260451 A1 | 9/2015 | Haberberger et al. | |
| 2015/0329445 A1 | 11/2015 | Kleiber et al. | |
| 2017/0010043 A1 | 1/2017 | Ducote, Jr. et al. | |
| 2017/0010443 A1 * | 1/2017 | Bone | G02B 13/0045 |
| 2018/0087832 A1 | 3/2018 | Roberts et al. | |
| 2019/0194094 A1 | 6/2019 | Jo et al. | |

FOREIGN PATENT DOCUMENTS

| | | |
|---|---|---|
| DE | 10110462 A | 9/2002 |
| WO | 2019194094 A1 | 10/2019 |
| WO | 2022008095 A1 | 1/2022 |

OTHER PUBLICATIONS

Chinese First Office Action for Application No. 201980066720.9 dated Aug. 9, 2022.

Barclay, et al., Enhanced Single Mixed Refrigerant Process For Stranded Gas Liquefaction, pp. PO-24.1-PO-24.10 (10 pages).

Bauer, Heinz, "Cryogenic Olefins Recovery From Dehydrogenation Reactor Effluents", AICHE Symposium on Cryogenic Gas Processing 1992 Spring National Meeting, Linde AG Munich, Germany, Jan. 1992, (16 pages).

Mafi, et al.,'Development in Mixed Refrigerant Cycles Used in Olefin Plants', Proceedings of the 1st Annual Gas Processing Symposium, Elsevier, vol. 1, 2009, (8 pages).

PCT Invitation to Pay Additional Fees And, Where Applicable, Protest Fee by the International Search Authority for International Application No. PCT/US2019/055170, dated Jan. 8, 2020, (16 pages).

* cited by examiner

DEHYDROGENATION SEPARATION UNIT WITH MIXED REFRIGERANT COOLING

CLAIM OF PRIORITY

This application is a Continuation of U.S. patent application Ser. No. 17/104,307, filed Nov. 25, 2020, which is a Continuation-in-Part of U.S. patent application Ser. No. 16/595,866, filed Oct. 8, 2019, which claims the benefit of U.S. Provisional Application No. 62/743,263, filed Oct. 9, 2018, the contents of each of which are hereby incorporated by reference.

BACKGROUND OF THE INVENTION

Propane Dehydrogenation (PDH) Separation Systems are known in the art. An example of such a system is described in commonly owned U.S. Pat. No. 6,333,445, the contents of which are incorporated herein by reference.

The current designs for PDH separation systems requires that the Reactor Effluent vapor stream be compressed to high pressure (~12 Barg) using the Reactor Effluent Compressor and then de-pressurized using two, generator-loaded or compressor-loaded, cryogenic turbo-expanders to provide the refrigeration required for the separation and recovery of the liquid olefin product.

Disadvantages of such prior art systems include power consumption of the overall process, the added cost and maintenance requirements of the turbo-expander/generator (or compressor) sets, the high required Reactor Effluent Compressor discharge pressure (which increases capital and operating costs) and lack of flexibility to significantly adjust the olefin and hydrogen separation temperatures.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a system for separating olefinic hydrocarbon and hydrogen in an effluent fluid stream from a dehydrogenation reactor includes a main heat exchanger configured to receive and partially condense the effluent fluid stream so that a mixed phase effluent stream is formed. A separation system is configured to receive and separate the mixed phase effluent stream into a separated vapor stream including hydrogen and a separated liquid stream including an olefinic hydrocarbon. A split is configured to receive and divide the separated vapor stream into a recycle gas stream and a net vapor stream. A junction is configured to receive a propane stream and the recycle gas stream so that a combined stream is formed. The main heat exchanger is configured to receive and warm the net vapor stream, the combined stream and the separated liquid stream to provide refrigeration in the main heat exchanger. A mixed refrigerant compression system configured to provide refrigeration in the main heat exchanger.

In another aspect, a method for separating olefinic hydrocarbon and hydrogen in an effluent fluid stream from a dehydrogenation reactor includes the steps of partially condensing the effluent fluid stream so that a mixed phase effluent stream is formed, separating the mixed phase effluent stream into a separated vapor stream containing hydrogen and a separated liquid stream containing an olefin product, dividing the separated vapor stream into a recycle gas stream and a net vapor stream, combining the recycle gas stream with a propane stream to form a combined stream, warming the net vapor stream, the combined stream, the separated liquid stream and a refrigerant stream to provide refrigeration for partially condensing the effluent fluid stream.

In another aspect, a system for separating an olefinic hydrocarbon and hydrogen in an effluent fluid stream from a dehydrogenation reactor includes a main heat exchanger configured to receive and partially condense the effluent fluid stream so that a mixed phase effluent stream is formed. A separation system is configured to receive and separate the mixed phase effluent stream into a separated vapor stream including hydrogen and a separated liquid stream including an olefinic hydrocarbon. A split is configured to receive and divide the separated vapor stream into a recycle gas stream and a net vapor stream. A junction is configured to receive a propane stream and the recycle gas stream so that a combined stream is formed. The main heat exchanger configured to receive and warm the net vapor stream, the combined stream and the separated liquid stream to provide refrigeration in the main heat exchanger. A refrigerant compression system is configured to provide refrigeration in the main heat exchanger.

In another aspect, a system for separating an olefinic hydrocarbon and hydrogen in an effluent fluid stream from a dehydrogenation reactor includes a main heat exchanger configured to receive and partially condense the effluent fluid stream so that a mixed phase effluent stream is formed. A separation device has a vapor outlet and a liquid outlet and is configured to receive and separate the mixed phase effluent stream into a vapor stream including hydrogen and a liquid stream including an olefinic hydrocarbon, where the vapor stream exits the separation device through the vapor outlet and the liquid stream exits the separation device through the liquid outlet. The main heat exchanger has a vapor passage in fluid communication with the vapor outlet of the separation device and a liquid passage in fluid communication with the liquid outlet of the separation device, wherein the vapor passage is configured to receive and warm at least a portion of the vapor stream to provide refrigeration in the main heat exchanger and the liquid passage is configured to receive and warm at least a portion of the liquid stream to provide refrigeration in the heat exchanger. A mixed refrigerant compression system is configured to provide refrigeration in the main heat exchanger.

DETAILED DESCRIPTION OF EMBODIMENTS

The present disclosure is directed to a dehydrogenation separation unit that here uses a Mixed Refrigerant (MR) system, consisting of a MR compressor with heat exchangers and drums (or other separation devices), to provide the refrigeration required for the separation and recovery of the liquid olefin product. As examples only, the MR system can either use a single mixed refrigerant system or be a single mixed refrigerant system that is pre-cooled using a second refrigerant. As examples only, the MR mixture may be made up substantially of methane, ethylene and/or ethane. While embodiments of the disclosure are described below as using a MR system, a single component refrigerant (such as nitrogen) may alternatively be used.

While achieving the same product recovery as prior art systems, some of the benefits may include: 1) the power consumption of the overall process is lower, 2) both turbo-expander/generator (or compressor) sets are eliminated, 3) the required Reactor Effluent Compressor discharge pressure is significantly reduced, which saves capital and operating costs, 4) the operation, maintenance and reliability of the Separation System is improved with the MR process compared to the turbo-expander process, 5) the MR process allows for a more robust and forgiving design of the main Feed Heat Exchanger, 6) the MR process provides an independent means to adjust the refrigeration level for the Separation System without impacting the Recycle Effluent Compressor.

Since propylene refrigeration is used in many PDH facilities, the MR process described herein uses propylene refrigeration to pre-cool the MR refrigerant and reduce the MR compressor power consumption. Pre-cooling also allows the MR component mix to be simplified, requiring only methane, ethylene (or ethane) and propylene (or propane), with ethylene and propylene being preferred. Without $C_4$ or $C_5$ in the MR mix, the possibility of reactor catalyst contamination is reduced.

While the explanation of the invention presented below is specific to a Propane Dehydrogenation Unit, the same process may be employed for Butane Dehydrogenation. In addition, when the term "drum" is used below, it is to be understood that any alternative separation device known in the art may be used instead.

Figure 1:
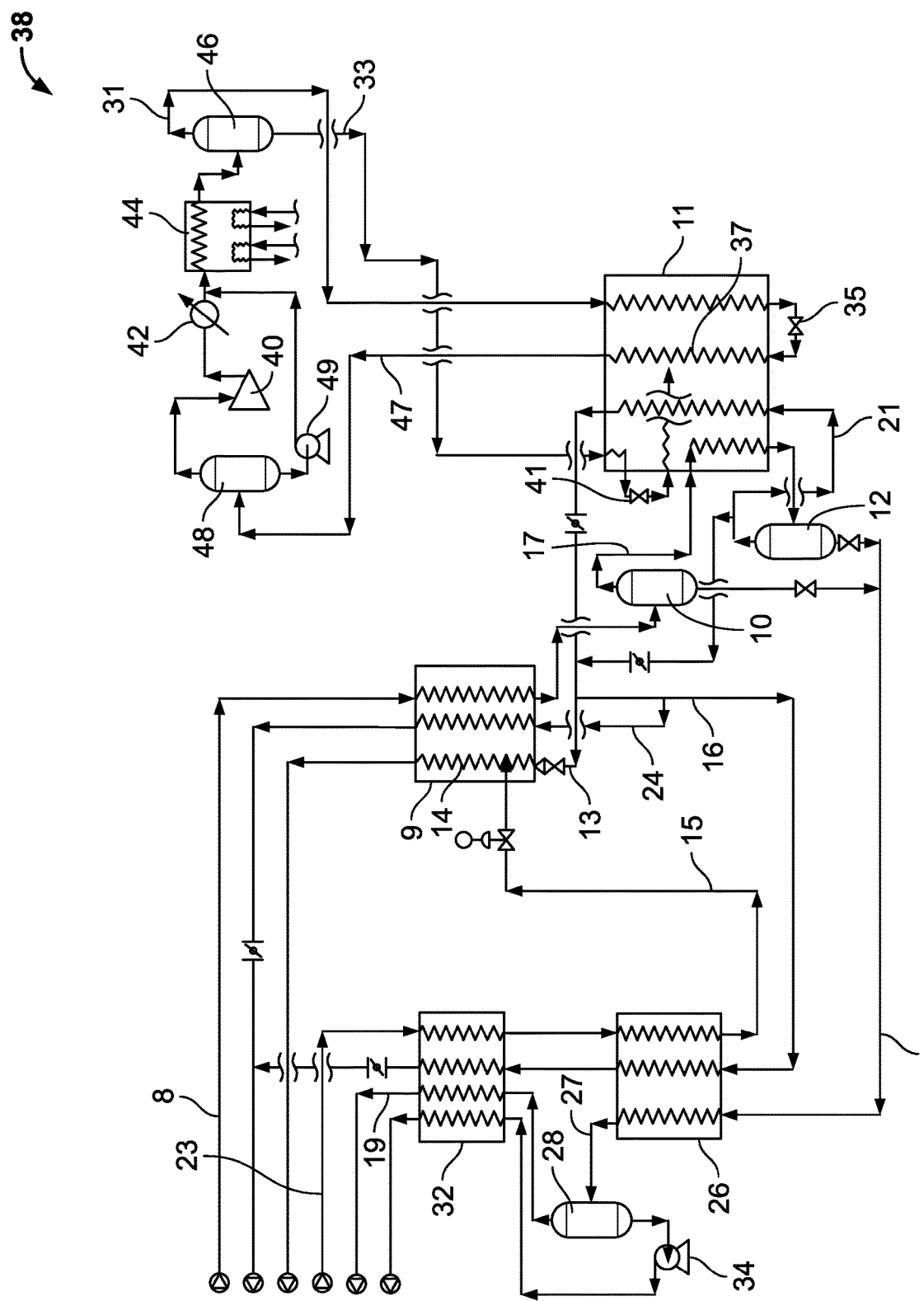
FIG. 1 is a schematic of a first embodiment of the system of the disclosure.

With reference to FIG. 1, Reactor Effluent Gas is compressed in the REC compressor to ~7.2 Barg and the heat of compression is removed prior to entering the cryogenic Separation System as the Cold Box Vapor Feed 8. The gas is sent to the Cold Box Feed Heat Exchanger 9, where it is partially condensed and then flows to an outlet Primary Separator 10. Vapor and liquid are separated, with the liquid stream containing a portion of the $C_3$ olefin product and a vapor stream 17 containing hydrogen and the remaining olefin product.

This vapor stream 17 flows to the Mixed Refrigerant Heat Exchanger 11 (MR exchanger), where it is further cooled to the required temperature and partially condensed to achieve the desired product recovery. The partially condensed stream flows to the Secondary Separator 12 and is separated into a liquid olefin product and a hydrogen rich vapor stream 21. The hydrogen rich stream is reheated in the MR exchanger and is then divided into two streams—Recycle Gas 13 (which is the hydrogen required for the Combined Reactor Feed) and Net Vapor, which is further divided into streams 16 and 24, which is the balance of the hydrogen stream and which will be exported from the Separation System.

Portion 16 of the Net Vapor stream is reheated and refrigeration recovered in a Fresh Feed Heat Exchanger (having cold end 26 and warm end 32). The liquid product streams (from the Primary and Secondary Separators 10 and 12) are combined to form combined liquid product stream 18 and flow to the Fresh Feed Heat Exchanger 26, 32.

The Cold Box Vapor Feed 8 ("Reactor Effluent") is cooled firstly in the Cold Box Feed Exchanger 9. It is cooled primarily by the Combined Reactor Feed 14 and secondarily by a portion 24 of the export Net Vapor Product. The Combined Reactor Feed 14 provides the bulk of the refrigeration, by combining the Recycle Gas stream 13 with a cold Fresh Feed liquid stream 15 (such as propane or n-butane) and vaporizing the combined stream in the Cold Box Feed Heat Exchanger 9. The cold Fresh Feed liquid stream 15 is formed from a Fresh Feed inlet stream 23 that is sub-cooled in the Fresh Feed Heat Exchanger at 26 and 32, before entering the Cold Box Feed Heat Exchanger 9. Refrigeration for the Fresh Feed is provided by recovering the cold from the C3 olefin product 18 and from a portion of the Net Vapor Product 16.

Flash Gas (recycle) 19 is produced by partially warming the separator liquids in the cold-end section 26 of the Fresh Feed Exchanger. The resulting vapor-liquid mix 27 is separated in the Liquid Product Tank 28. The vapor from tank 28 is warmed in the warm-end section 32 of the Fresh Feed Exchanger and the Flash Gas 19 is recycled to the suction of the upstream Reactor Effluent Compressor (see FIG. 1 of U.S. Pat. No. 6,333,445). The Liquid Product from tank 28 is pumped via pump 34 and additional cold is recovered in the warm-end section 32 of the Fresh Feed Exchanger.

The overall refrigeration balance for the Separation System is provided by the Mixed Refrigerant (MR) compression system, indicated in general at 38 in FIG. 1, via the final cooling in the MR Exchanger (MRHX) 11. A $C_3$ pre-cooled MR system is described here; however, a single MR system may also be used. FIG. 1 shows a single-stage MR Compressor 40, followed by an air or water cooler 42, and then followed by a $C_3$ (propylene) pre-cooler 44. The pre-cooler can utilize as many stages of refrigeration as required to obtain the desired temperature, two stages are shown for simplicity. The MR refrigerant is separated via separator 46 into vapor and liquid phase streams 31 and 33, respectively, and sent to the MRHX 11. The MR vapor stream 31 is cooled and condensed in the MRHX 11 and is flashed at 35 to create the coldest refrigerant for the process and the low pressure refrigerant stream 37. The MR liquid stream 33 is also cooled in the MRHX, flashed at 41 and sent to the low pressure refrigerant stream 37, where it joins and is mixed with the low pressure refrigerant stream 37 at a warmer temperature. The common refrigerant return stream 47 exits the MRHX 11 as a mixed phase vapor/liquid stream. Before being compressed, the vapor and liquid are separated via separator 48. The liquid is pumped via pump 49 to higher pressure and the vapor is compressed at compressor 40 to the required discharge pressure. The system uses an MR composition suitable for the specific design conditions.

The heat exchangers illustrated in FIG. 1 and described above may be incorporated or integrated into a single main heat exchanger.

Figure 2:
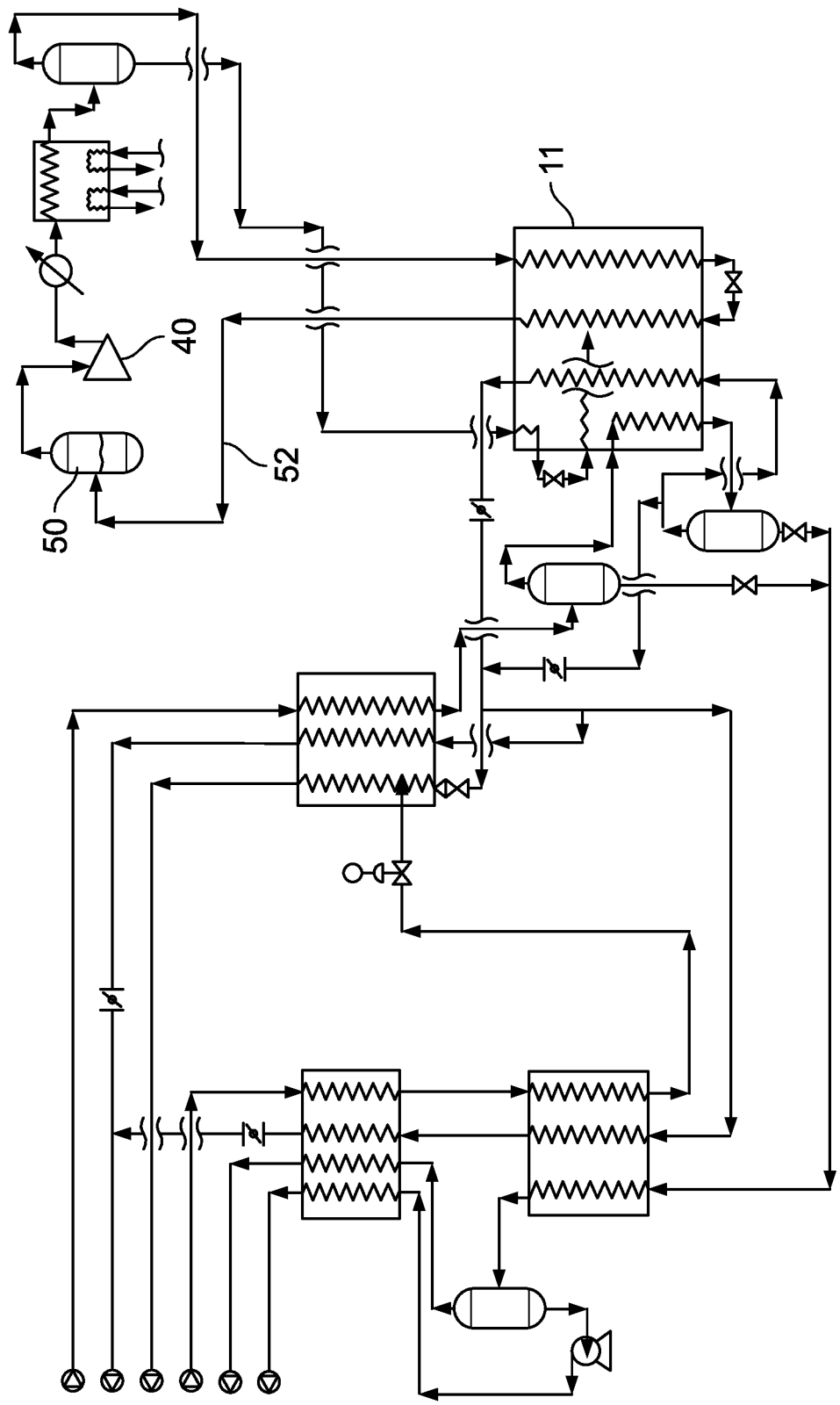
FIG. 2 is a schematic of a second embodiment of the system of the disclosure.

With reference to FIG. 2, in a second embodiment of the system, the suction drum to the MR Compressor can also be designed to act as a heavy component refrigerant accumulator. The MR system may be operated with excess heavy components (such as $C_3$, $C_4$ or $C_5$) in the refrigerant and with the resulting MR being, at least temporarily, a 2-phase stream 52 exiting the exchanger 11. These excess heavy components are separated in the compressor suction drum 50 and remain in the drum. The refrigerant vapor, which flows to the MR Compressor 40, is now at its dew point and the system operates automatically at the dew point condition. As "make up" refrigerant is added to the system, the accumulated heavy components will then equilibrate with light components to the dew point at suction pressure and temperature. If needed, the heavy components can be preferentially removed from the refrigeration system at the suction accumulator or preferentially added and retained in the suction drum.

Figure 3:
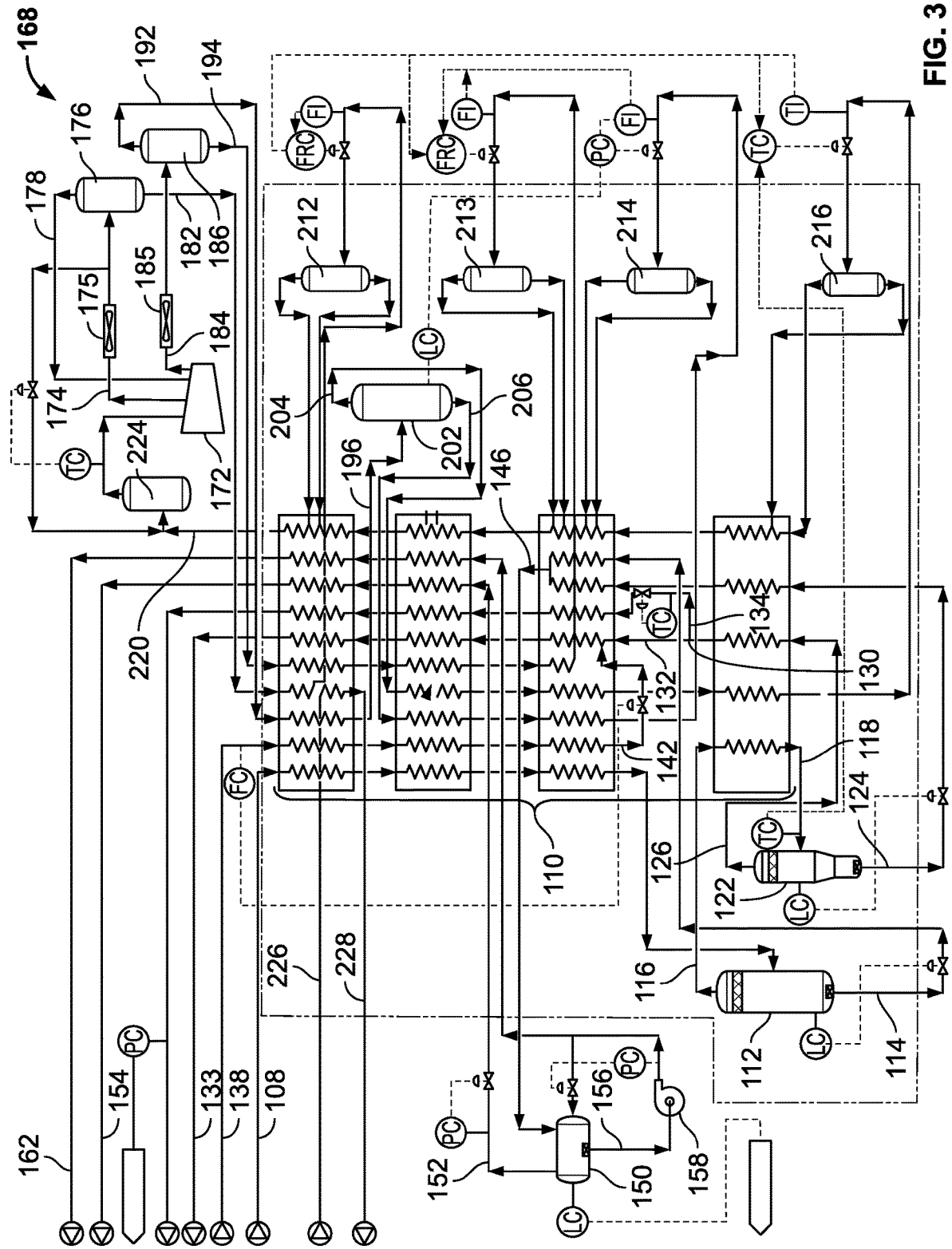
FIG. 3 is a schematic of a third embodiment of the system of the disclosure.

In a third embodiment of the system, illustrated in FIG. 3, Reactor Effluent Gas is compressed in the REC compressor to ~7.2 Barg and the heat of compression is removed via ambient exchanger (air or water) cooling prior to entering the Cryogenic Separation System as the Cold Box Vapor Feed 108. The gas is sent to the Main Heat Exchanger 110, where it is cooled and partially condensed and then flows to the Primary Separator 112. Vapor and liquid are separated, with the liquid stream 114 containing a portion of the C3 olefin product and the vapor stream 116 containing hydrogen and the remaining olefin product. This vapor stream flows back to the Main Heat Exchanger 110, where it is further cooled and partially condensed to achieve the desired product recovery. The partially condensed stream 118 flows to the Secondary Separator 122 and is separated into a liquid olefin product 124 and a hydrogen rich stream 126. The hydrogen rich vapor stream is reheated in the Main Heat Exchanger and is then divided at 130 into two streams—Recycle Gas 132 (which is the hydrogen required for the Combined Reactor Feed 133) and Net Vapor 134 (which is the remaining balance of the hydrogen stream and will be exported from the Separation System). The Net Vapor stream is reheated and the refrigeration is recovered in the Main Heat Exchanger.

Warm fresh propane feed 138 is sent to the Main Heat Exchanger 110, and cooled to approximately the same temperature as the Primary Separator 112. The cooled fresh propane feed 142 is then mixed with the Recycle Gas 132 to form the Combined Reactor Feed 133. This stream is reheated, and the refrigeration is recovered in the Main Heat Exchanger. This provides the majority of the refrigeration for the cryogenic separation system.

The liquid product streams 114 and 124 (from the Primary and Secondary Separators 112 and 122) are fed to the Main Heat Exchanger 110 at an appropriate location relative to their respective temperature. The liquid product streams are heated, and partially vaporized. The liquid product streams exit the Main Heat Exchanger thru a common header to form liquid product stream 146. This orientation of the liquid product streams improves efficiency, reduces piping complexity, and lowers the risk of freezing.

The partially vaporized mixed C3 liquid product stream 146 is sent to the Liquid Product Tank 150. The vapor 152 from the Liquid Product Tank (Flash Gas) is heated in the Main Heat Exchanger and then recycled to the suction of the upstream Reactor Effluent Compressor as Flash Gas Stream 154. The liquid 156 from the Liquid Product Tank (Liquid Product) is pumped via pump 158, and then heated in the Main Heat Exchanger for additional energy recovery. The warmed Liquid Product exits the Main Heat Exchanger as C3 Product stream 162.

The overall refrigeration balance for the Separation System is provided by a Mixed Refrigerant (MR) system, indicated in general at 168. The embodiment of FIG. 3 uses a two-stage MR Compressor 172, with air or water intercooling and discharge cooling. The discharge 174 of the first MR Compressor Stage is partially condensed at 175, and sent to the MR Interstage Drum 176. The vapor 178 is sent to the Second MR Compressor Stage, and the liquid 182 is sent to the Main Heat Exchanger 110. The second MR Compressor Stage Discharge 184 is partially condensed at 185, and separated in the MR Accumulator 186. The MR Accumulator Vapor 192 and Liquid 194 are sent to the Main Heat Exchanger 110. The MR Accumulator Vapor is partially condensed in the Main Heat Exchanger, and the resulting stream 196 is sent to a Cold Vapor Separator Drum 202 in order to improve the process efficiency. The Cold Vapor Separator Vapor 204, Cold Vapor Separator Liquid 206, MR Accumulator Liquid 194, and MR Interstage Liquid 182 are all condensed and subcooled in the Main Heat Exchanger 110. All of these streams exit the exchanger, are flashed across JT Valves (as an example only), and the resulting mixed phase streams separated and sent back to the Main Heat Exchanger via standpipes 212, 213, 214 and 216 at the appropriate temperatures to provide the refrigeration balance required for the separation system. Additional details regarding operation of the MR system 168 are available in commonly owned U.S. Pat. No. 10,480,851 to Ducote, Jr. et al., the entire contents of both of which are hereby incorporated by reference.

The flashed low pressure MR streams are mixed within the Main Heat Exchanger and exit as a single superheated vapor stream 220 which is sent to the MR Compressor Suction Drum 224. The system uses an MR composition suitable for the specific design conditions.

The MR system allows for the integration of additional heat transfer services that are at ambient temperature or cooler into the Main Heat Exchanger. As an example, FIG. 3 shows the integration of the Deethanizer Rectifier Condenser (deethanizer overhead inlet stream 226 and deethanizer overhead outlet stream 228) into the Main Heat Exchanger. This increases the size of the MR system due to the additional refrigeration duty that is required, but removes the need for a separate C3 refrigeration system for the Deethanizer Rectifier Condenser service which reduces overall equipment count for the dehydrogenation plant.

Figure 4:
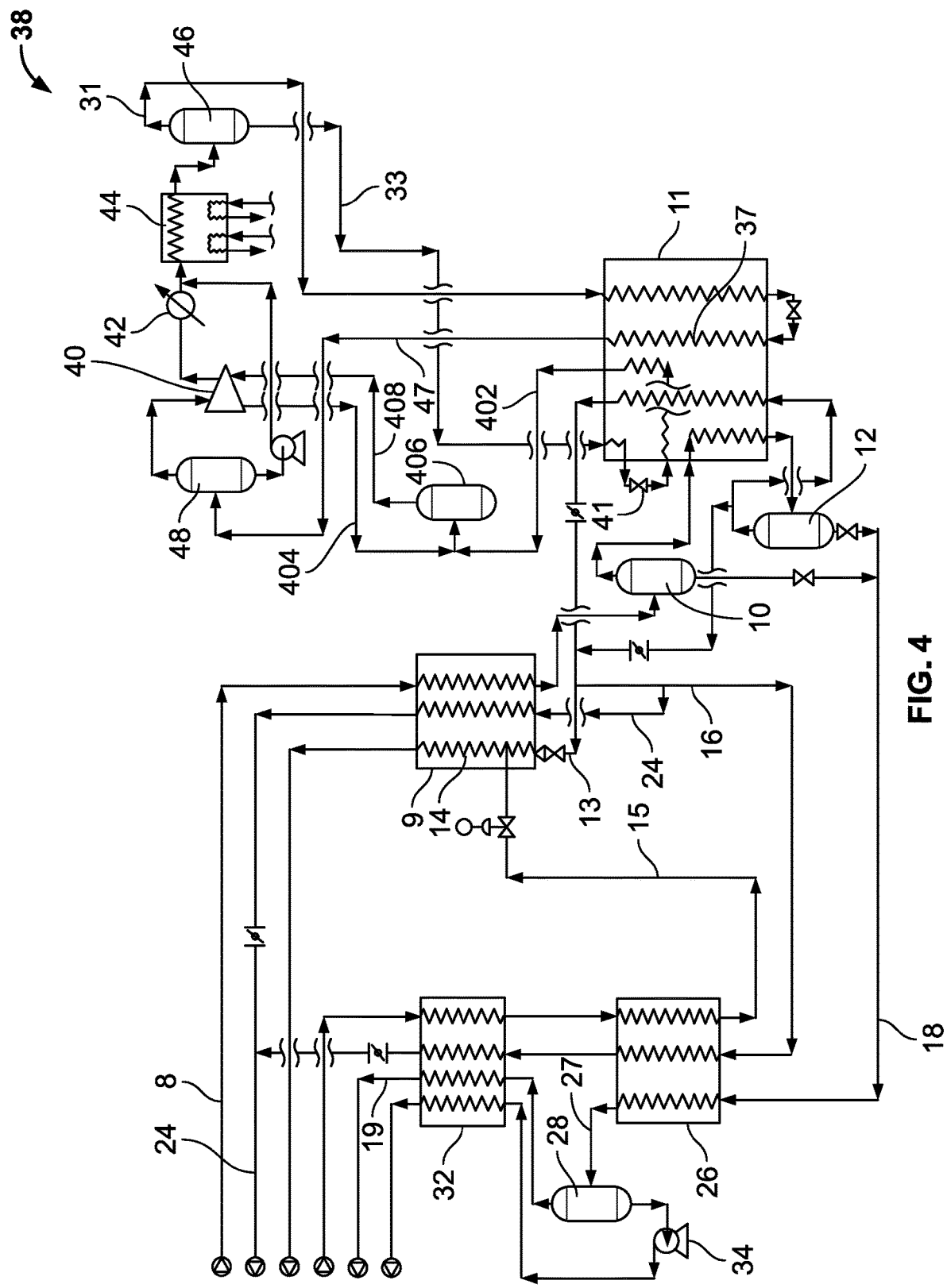
FIG. 4 is a schematic of a fourth embodiment of the system of the disclosure.

In a fourth embodiment of the system of the disclosure, illustrated in FIG. 4, an interstage separation device 406 is added to the system of FIG. 1. A mixed phase MR stream 402, from a secondary refrigeration passage of the MR heat exchanger 11 (which receives a stream that originated as the liquid outlet of separator 46 prior to entering the MR heat exchanger), is combined with a mixed phase MR stream 404 from the outlet of the first stage of compressor 40. The combined stream is directed to the inlet of separation device 406 and the resulting vapor stream 408 is directed into the inlet of the second stage of compressor 40. The outlet of the second stage of compressor 40 is directed to cooling devices 42 and 44, and processing of the MR stream then continues as described above with respect to FIG. 1, with the exception that stream 33, after cooling in mixed refrigerant heat exchanger 11 and flashing via valve 41, does not join with the low pressure refrigerant stream 37. In alternative embodiments, however, a portion of the stream 33, after cooling in mixed refrigerant heat exchanger 11 and flashing via valve 41, may join the low pressure refrigerant stream 37.

Figure 5:
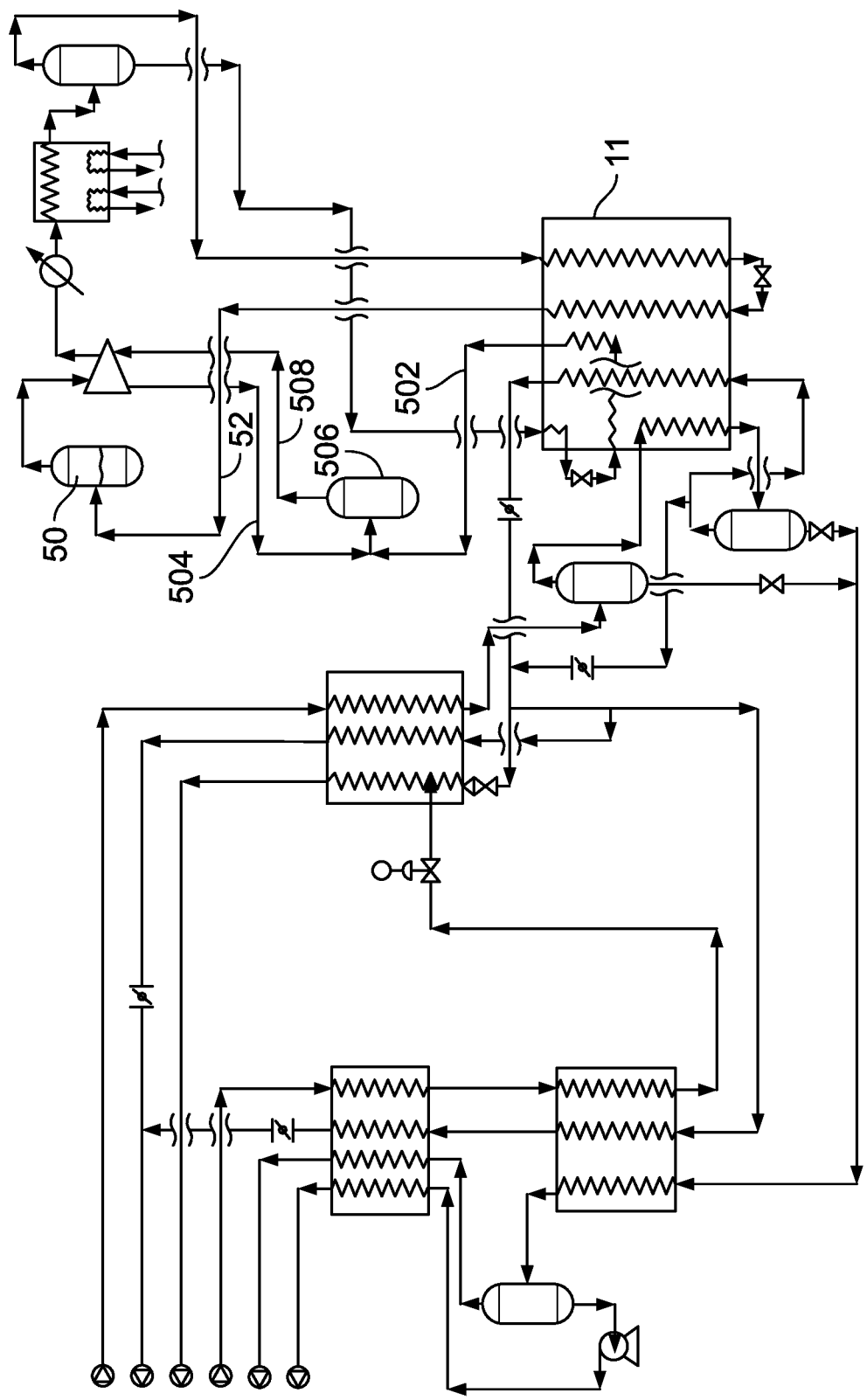
FIG. 5 is a schematic of a fifth embodiment of the system of the disclosure.

In a fifth embodiment of the system of the disclosure, illustrated in FIG. 5, an interstage separation device 506 is added to the system of FIG. 2. A mixed phase MR stream 502, from MR heat exchanger 11, is combined with a mixed phase MR stream 504 from the outlet of the first stage of a MR compressor. The combined stream is directed to the inlet of separation device 506 and the resulting vapor stream 508 is directed into the inlet of the second stage of the MR compressor. The outlet of the second stage of the MR compressor is directed to one or more cooling devices, and processing of the MR stream then continues as described above with respect to FIG. 4.

The referenced heat exchangers in the description may be combined, with the use of multi-stream heat exchangers, such as Brazed Aluminum Plate Fin heat exchangers, to simplify the piping design, plant layout or performance. Examples of combinations may be the Fresh Feed-1 Exchanger with the Fresh Feed-2 Exchangers or both Fresh Feed Exchangers with the Cold Box Feed Exchanger. Other combinations may also be desirable.

Figure 6:
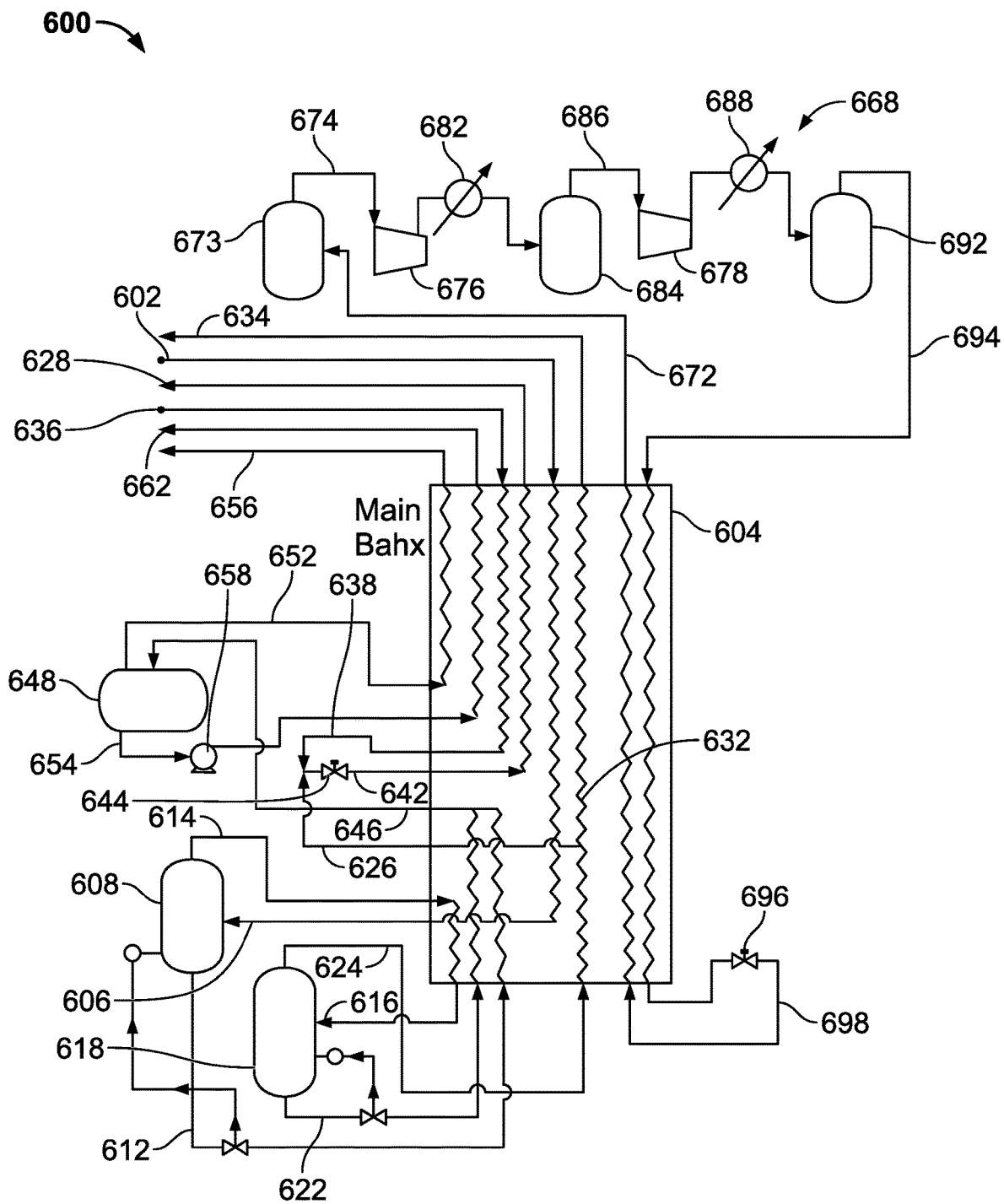
FIG. 6 is a schematic of a sixth embodiment of the system of the disclosure.

In a sixth embodiment of the system of the disclosure, indicated in general at 600 in FIG. 6, a reactor effluent gas stream 602 is directed to a main heat exchanger 604, where it is cooled and partially condensed. As examples only (for the embodiment of FIG. 6 and other embodiments), the reactor effluent gas stream 602 may be a mixture of propylene, propane and hydrogen, a mixture of isobutylene, isobutane and hydrogen or a mixture of propylene, isobutylene, propane, isobutane and hydrogen. The resulting mixed-phase stream 606 flows to a primary separator 608 wherein vapor and liquid are separated, with a resulting liquid stream 612 containing a portion of a C3 olefin product and a resulting vapor stream 614 containing hydrogen and the remaining olefin product. Vapor stream 614 flows back to the main heat exchanger 604, where it is further cooled and partially condensed. The resulting partially condensed stream 616 flows to the secondary separator 618 and is separated into a liquid olefin product 622 and a hydrogen rich vapor stream 624. The hydrogen rich vapor stream 624 is reheated in the main heat exchanger and is then divided into two streams—recycle gas stream 626 (which is the hydrogen required for the combined reactor feed stream 628) and net vapor stream 632 (which is the remaining balance of the hydrogen stream). The net vapor stream is reheated in the main heat exchanger 604, so that the refrigeration is recovered, and directed out of the main heat exchanger and system as stream 634.

Warm fresh propane feed 636 is sent to the main heat exchanger 604, and cooled to approximately the same temperature as the primary separator 608. The cooled fresh propane feed 638 is then combined or mixed with the recycle gas 626 and the combined stream is expanded via expansion device 644 to form stream 642. Stream 642 is reheated so that the refrigeration is recovered in the main heat exchanger. This provides the majority of the refrigeration for the cryogenic separation system. The resulting reheated stream exits the main heat exchanger and separation system as combined reactor feed stream 628.

The liquid product streams 612 and 622 (from the primary and secondary separators 608 and 618) are fed to the main heat exchanger 60 wherein they are heated, partially vaporized and combined. The resulting mixed phase product stream 646 exits the main heat exchanger and is directed to a product tank 648 so that product vapor stream 652 and product liquid stream 654 are produced.

The vapor 652 from the product tank 648 (flash gas) is heated in the main heat exchanger and then exits the separation system as flash gas stream 656. The liquid stream 654 from the product tank is pumped via pump 658 and then heated in the main heat exchanger for additional refrigeration recovery. The warmed liquid exits the main heat exchanger as a product stream 662.

The overall refrigeration balance for the separation system 600 of FIG. 6 is provided by a mixed refrigerant system, indicated in general at 668. Mixed refrigerant (MR) exits the main heat exchanger 604 as stream 672 after providing cooling therein. This stream is received by a separation device such as suction drum 673 so that any liquid remaining in stream 672 is removed before vapor MR stream 674 is provided to a first MR compressor stage 676. The suction drum 673 may optionally be provided with a liquid outlet leading to a pump so that liquid from the suction drum 673 may be pumped down stream to the discharge pressure of compressor stage 676, as illustrated in the embodiment of FIG. 1 (where the pump is illustrated at 49).

While the embodiment of FIG. 6 uses a single two-stage MR compressor to provide first (676) and second (678) compressor stages, two separate compressors may instead be used to form the first and second stages. In addition, the mixed refrigerant system 668 may use an alternative number of compression and cooling stages with intercooling and discharge cooling.

The discharge of the first MR compressor stage 676 is cooled and partially condensed by after-cooler 682 (which, as an example only, may provide cooling via air or water), and sent to a separation device such as an MR interstage drum 684. A vapor stream 686 exits the interstage drum 684 and is sent to a second MR compressor stage 678. The discharge of second MR compressor stage 678 is cooled by after-cooler 688 with the resulting cooled vapor stream directed to a separation device such as discharge drum 692.

The vapor stream 694 from the discharge drum 692 is sent to the main heat exchanger 604 where it is condensed and subcooled and then flashed across an expansion device 696 (such as a Joule-Thomson/JT valve or other type of expansion valve or device known in the art). The resulting mixed-phase stream 698 is directed to the main heat exchanger where it serves as the primary MR refrigeration stream in the main heat exchanger at the appropriate temperature to provide the refrigeration balance required for the separation system.

Precooling of the mixed refrigerant may be done within the core of the main heat exchanger 604 to eliminate the need for a separate propane or mechanical refrigeration system to cool the mixed refrigerant after the final stage of compression.

In the embodiment of FIG. 6, preferably no liquids are produced at the suction drum 673, the interstage drum 684 or the discharge drum 692. This is due maintaining the mixed refrigerant below the dew point of the mixture during the compression cycle. By not producing liquids, liquids do not have to be pumped or handled in the process simplifying the process and decreasing the costs.

It is to be understood that, in the system of FIG. 6, and the systems described below, that alternative types of separation devices known in the art may be substituted for each of the suction drum 673, the interstage drum 684 and/or the discharge drum 692.

In some applications, the mixed refrigerant composition of the system of FIG. 6 is primarily made up of methane, ethylene, and propylene. Ethane can be substituted for the ethylene and propane can be substituted for propylene. Refrigerants are generally readily available as part of the propylene dehydrogenation process as a by-product of the process, making them easy to source.

While the embodiment of FIG. 6 features a single main heat exchanger 604, multiple heat exchangers may be used instead. Using a single heat exchanger, however, reduces equipment count and two-phase distribution concerns. In addition, having the ability to perform this process in a single heat exchanger provides for improved heat transfer between all streams in the process thereby improving efficiency.

Using a mixed refrigerant (instead of mechanical refrigeration) in the system of FIG. 6 may provide improved overall process efficiency, allow for colder separator temperatures, and independent temperature control. In addition, using a mixed refrigerant (instead of cascade refrigeration) may provide improved efficiency and allow for colder separator temperatures with significantly lower equipment counts.

In alternative embodiments compression in the system of FIG. 6 can be performed using a single stage process without intercooling.

Figure 7:
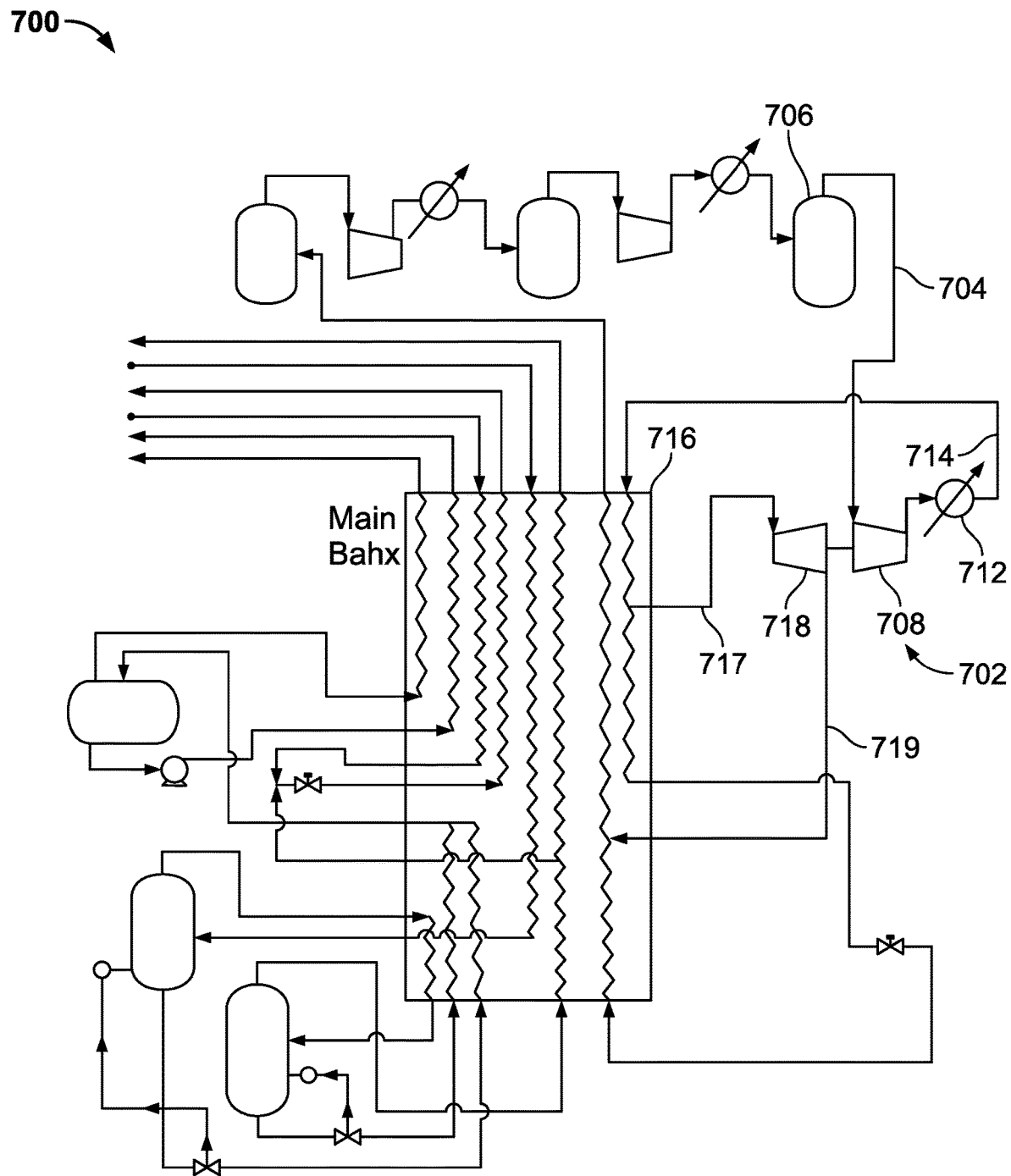
FIG. 7 is a schematic of a seventh embodiment of the system of the disclosure.

In a seventh embodiment of the system of the disclosure, indicated in general at 700 in FIG. 7, a first or "warm" turbo-expander, indicated in general at 702, has been added to the system of FIG. 6. More specifically, the vapor stream 704 exiting the discharge drum 706 enters a compressor 708, where it is compressed. The compressed vapor stream exiting the compressor 708 is directed to after-cooler 712 (which, as examples only, may be air or water cooled) for cooling, and the resulting stream 714 is directed to the main heat exchanger 716 for further cooling. A compressed and cooled stream 717 branches off of stream 714 and exits the main heat exchanger 716. Stream 717 enters turbine 718 and is expanded with the resulting cooled stream 719 directed to the primary MR refrigeration passage of the main heat exchanger.

As illustrated in FIG. 7, the turbine 718 is mechanically linked to the compressor 708 so that the expansion energy recovered by the turbine 718 may be used to drive the compressor 708. As a result, the turbo-expander recovers energy from the expansion process used to reduce the temperature of the refrigerant to provide an additional compression stage. In an alternative embodiment, the recovered expansion energy may instead be used to generate electricity or for another process.

The remaining components of the system of FIG. 7 operate in the same manner as those illustrated in, and described with respect to, FIG. 6.

Figure 8:
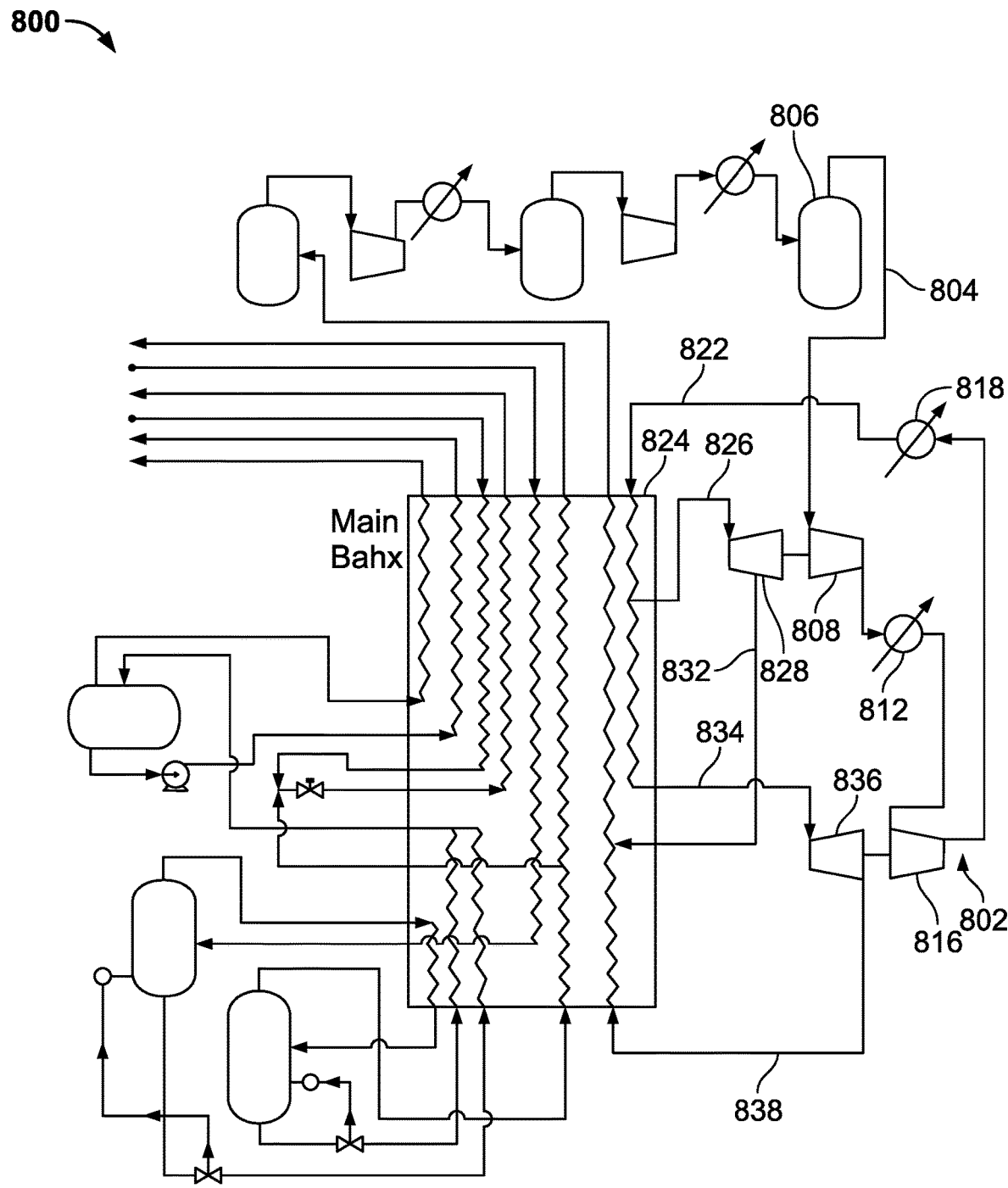
FIG. 8 is a schematic of an eighth embodiment of the system of the disclosure.

In an eighth embodiment of the system of the disclosure, indicated in general at 800 in FIG. 8, a second or "cold" turbo-expander, indicated in general at 802, has been added to the system of FIG. 7. In this system, the vapor stream 804 exiting the discharge drum 806 enters a compressor 808 of a warm turbo-expander, where it is compressed. The compressed vapor stream exiting the compressor 808 is directed to after-cooler 812 (which, as examples only, may be air or water cooled) for cooling, and the resulting stream 814 is directed to the compressor 816 of the cold turbo-expander. The stream exiting compressor 816 is directed to after-cooler 818 (which, as examples only, may be air or water cooled) for cooling, and the resulting stream 822 is directed to the main heat exchanger 824 for further cooling. A first compressed and cooled stream 826 branches off of stream 822 and exits the main heat exchanger 824. Stream 826 enters the turbine 828 of the warm turbo-expander and is expanded with the resulting cooled stream 832 directed to the primary MR refrigeration passage of the main heat exchanger. A second compressed and cooled stream 834 branches off of stream 822 and exits the main heat exchanger 824. Stream 834 enters the turbine 836 of the cold turbo-expander and is expanded with the resulting cooled stream 838 directed to the primary MR refrigeration passage of the main heat exchanger.

In view of the above, the warm and cold turbo-expanders recover energy from expansion processes used to reduce the temperature of the refrigerant to provide additional compression stages. In alternative embodiment the recovered energy from either expansion or both expansions may be used to generate electricity or for other processes.

In the system of FIG. 8, the refrigerant can be a mixed refrigerant or a single refrigerant, such as nitrogen. Nitrogen can also be part of a refrigerant mixture primary made up of nitrogen and hydrocarbons.

The cold turbo-expander 802 may be eliminated or bypassed using one or more bypass valves and/or bypass lines.

The remaining components of the system of FIG. 8 operate in the same manner as those illustrated in, and described with respect to, FIG. 6.

Figure 9:
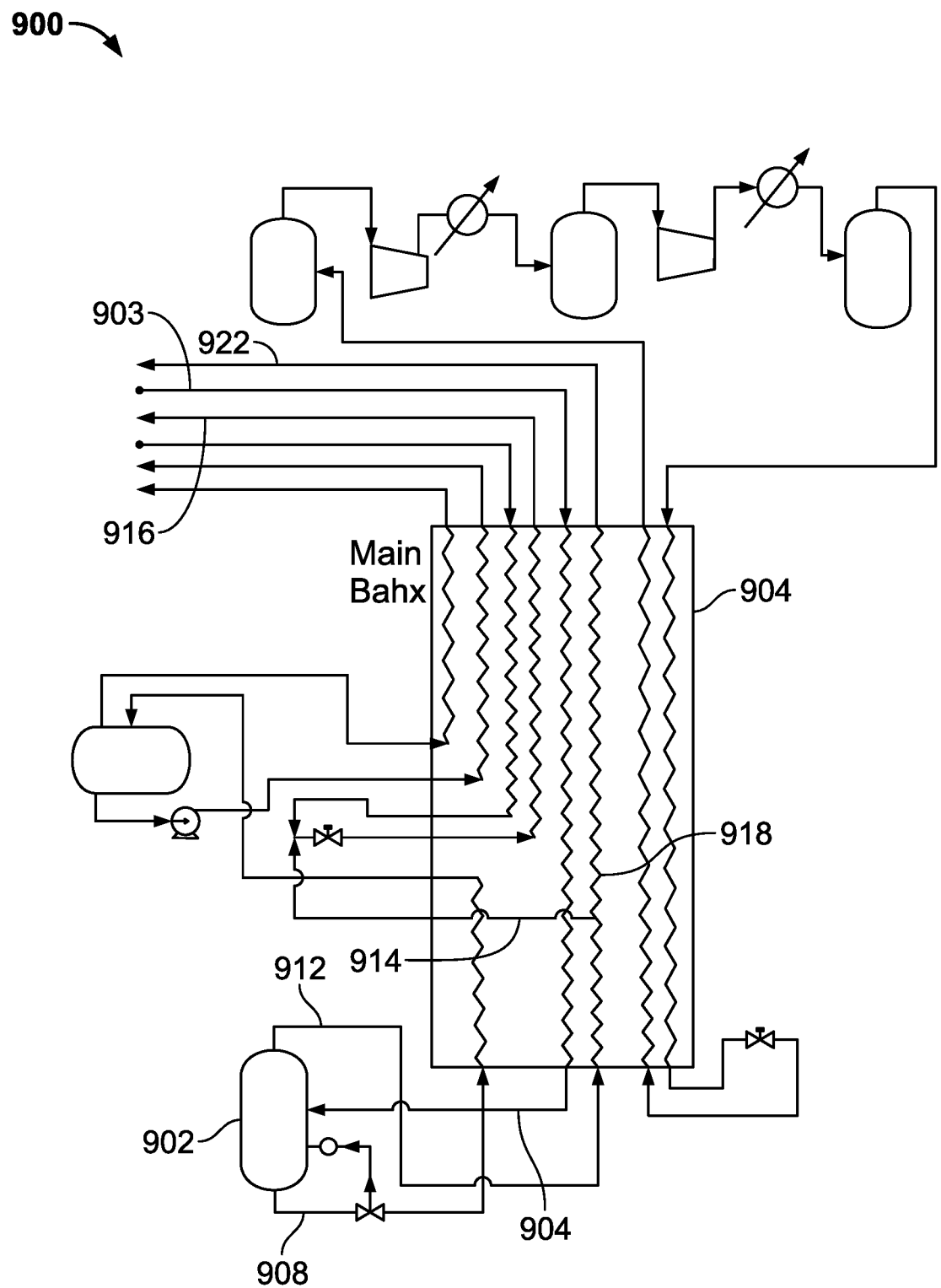
FIG. 9 is a schematic of a ninth embodiment of the system of the disclosure.

In a ninth embodiment of the system of the disclosure, indicated in general at 900 in FIG. 9, a single separation device or separator 902 may be used instead of the primary and secondary separators 608 and 618 of FIG. 6.

In the system of FIG. 9, as in the system of FIG. 6, a reactor effluent gas stream 903 is directed to a main heat exchanger 904, where it is cooled and partially condensed. The resulting mixed-phase stream 906 flows to a separator 902 wherein vapor and liquid are separated, with a resulting liquid stream 908 containing an olefin product and a resulting vapor stream 912 containing hydrogen. Vapor stream 912 flows back to the main heat exchanger 904, where it is reheated and divided into two streams—recycle gas stream 914 (which is the hydrogen required for the combined reactor feed stream 916) and net vapor stream 918 (which is the remaining balance of the hydrogen stream). The net vapor stream 918 is reheated in the main heat exchanger 904, so that the refrigeration is recovered, and directed out of the main heat exchanger and system as stream 922.

While using a single separator 902 reduces the pieces of equipment and lowers the capital costs, efficiency of the process may suffer.

The remaining components of the system of FIG. 9 operate in the same manner as those illustrated in, and described with respect to, FIG. 6.

Figure 10:
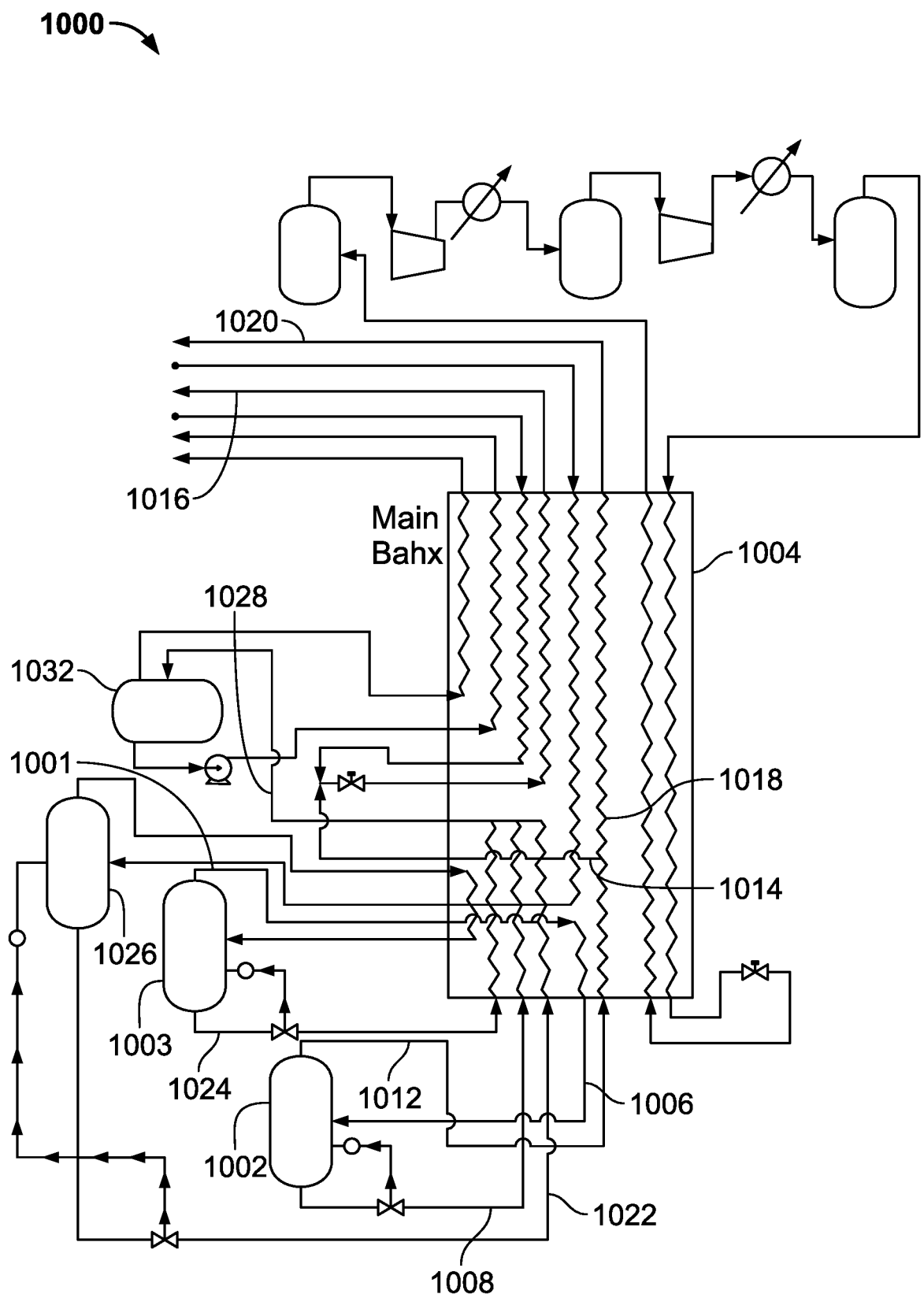
FIG. 10 is a schematic of a tenth embodiment of the system of the disclosure.

In a tenth embodiment of the system of the disclosure, indicated in general at 1000 in FIG. 10, a tertiary separation device or separator 1002 has been added to the system of FIG. 6. More specifically, in the embodiment of FIG. 10, a vapor stream 1001 flows from the secondary separator 1003 into the main heat exchanger 1004. The resulting mixed-phase stream 1006 flows to the tertiary separator 1002 wherein vapor and liquid are separated into a liquid olefin product 1008 and a hydrogen rich vapor stream 1012. The hydrogen rich vapor stream 1012 is reheated in the main heat exchanger and is then divided into two streams—recycle gas stream 1014 (which is the hydrogen required for the combined reactor feed stream 1016) and net vapor stream 1018 (which is the remaining balance of the hydrogen stream). The net vapor stream is reheated in the main heat exchanger 1014, so that the refrigeration is recovered, and directed out of the main heat exchanger and system as stream 1020.

The liquid product stream 1008 is combined with liquid product streams 1022 and 1024 (from the primary and secondary separators 1026 and 1003) are fed to the main heat exchanger 1004 wherein they are heated, partially vaporized and combined. The resulting mixed phase product stream 1028 exits the main heat exchanger and is directed to a product tank 1032.

The remaining components of the system of FIG. 10 operate in the same manner as those illustrated in, and described with respect to, FIG. 6.

The separation process of FIG. 6 therefore can be carried out using three separation vessels, as illustrated in FIG. 10, instead of one or two separation vessels. This process improves the separation efficiency of the process though increases the total equipment pieces.

Figure 11:
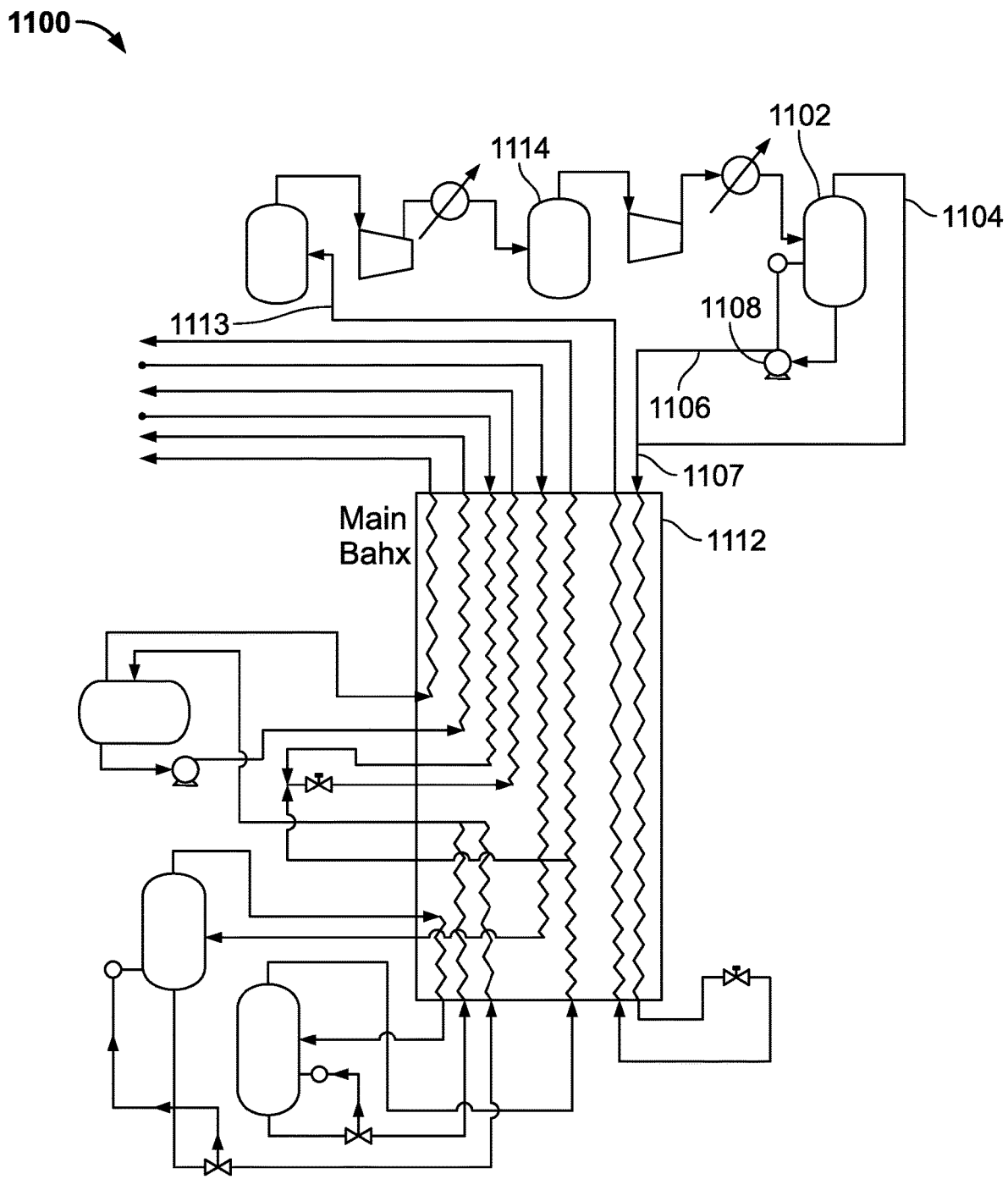
FIG. 11 is a schematic of an eleventh embodiment of the system of the disclosure.

In an eleventh embodiment of the system of the disclosure, indicated in general at 1100 in FIG. 11, it is recognized that modifications to the mixed refrigerant, discharge pressure of the second compressor stage, and/or cooling temperature may cause liquids to be formed in the discharge drum 1102 of the compressor. This liquid can be combined with the vapor stream 1104 via line 1106 at junction 1107. Line 1106 may be provided with a pump 1108 or a valve to control the flow of liquid from the discharge drum 1102 to the junction 1107 and thus to vapor stream 1104.

Forming liquids in the discharge drum 1102 can create advantages when additional loads are desired to be included into the main heat exchanger 1112. These additional loads would likely come from different processes of the larger dehydrogenation process. An example would be the integration of a deethanizer rectifier condenser. The liquid stream (in line 1106 of FIG. 11) may be combined with the vapor stream 1104, as shown in FIG. 11, or it may also be sent to its own heat transfer path within the main heat exchanger 1112. When sent to its own heat transfer path, the liquid stream (from line 1106) could be combined with the low pressure vapor return stream 1113 after flashing the liquid stream to the lower pressure of the return stream.

Liquids may also be formed in the interstage drum 1114, which may be dealt with in a similar manner as described above for discharge drum 1102 and for the same reasons as liquids that form in the discharge drum The remaining components of the system of FIG. 11 operate in the same manner as those illustrated in, and described with respect to, FIG. 6.

In an alternative embodiment, the system of FIG. 11 may instead be configured so that the vapor and liquid streams 1104 and 1106 exiting discharge drum 1102 are individually cooled in dedicated passages of the heat exchanger 1112, individually expanded across dedicated expansion devices (such as Joule-Thomson/JT valves or other type of expansion valves or devices known in the art) and then directed to the primary refrigeration passage of the heat exchanger 1112 (as shown in the embodiment of FIG. 1) or dedicated refrigeration passages of the heat exchanger 1112 (as shown in the embodiment of FIG. 4). In addition, in the latter embodiment (dedicated heat exchanger refrigeration passages as shown in FIG. 4), the outlet of the dedicated refrigeration passage corresponding to the liquid stream 1106 of the discharge drum 1102 may be directed to interstage drum 114 (as illustrated at 406 in FIG. 4).

While the preferred embodiments of the invention have been shown and described, it will be apparent to those skilled in the art that changes and modifications may be made therein without departing from the scope of the invention.

What is claimed is:

1. A system for separating olefinic hydrocarbon and hydrogen in an effluent fluid stream from a dehydrogenation reactor comprising:
   a. a main heat exchanger configured to receive and partially condense the effluent fluid stream so that a mixed phase effluent stream is formed;
   b. a separation system configured to receive and separate the mixed phase effluent stream into a separated vapor stream including hydrogen and a separated liquid stream including an olefinic hydrocarbon;
   c. a split configured to receive and divide the separated vapor stream as a single phase vapor stream into a recycle gas stream and a net vapor stream, wherein both of the recycle gas stream and the net vapor stream are single phase vapor streams;
   d. a junction configured to receive and combine a propane stream, where the propane stream is independent of the effluent stream, and at least a portion of the recycle gas stream so that a combined stream is formed;
   e. said main heat exchanger configured to receive and warm the net vapor stream, the combined stream and the separated liquid stream to provide refrigeration in the main heat exchanger;
   f. a mixed refrigerant compression system configured to provide refrigeration in the main heat exchanger.

2. The system of claim 1 wherein the main heat exchanger includes a primary refrigeration passage and the mixed refrigerant compression system includes:
   i) a suction separation device configured to receive a mixed phase refrigerant stream from the primary refrigeration passage of the main heat exchanger;
   ii) a compressor having an inlet in fluid communication with the suction separation device;
   iii) a first stage cooling device having an inlet in fluid communication with an outlet of the compressor;
   iv) a discharge separation device having an inlet in fluid communication with an outlet of the first stage cooling device and a vapor outlet in fluid communication with the primary refrigeration passage of the main heat exchanger.

3. The system of claim 2 further comprising a second stage cooling device and wherein the compressor is a two-stage compressor including a first stage having a compressor first stage inlet in fluid communication with an outlet of the suction separation device so that the compressor first stage inlet receives fluid from the outlet of the suction separation device and a compressor first stage outlet in fluid communication with an inlet of the first stage cooling device so that the inlet of the first stage cooling device receives fluid from the compressor first stage outlet, an interstage separation device having an interstage separation device inlet in fluid communication with an outlet of the first stage cooling device so that the interstage separation device inlet receives fluid from the outlet of the first stage cooling device, the compressor also including a second stage having a compressor second stage inlet in fluid communication with an interstage separation device outlet of the interstage separation device so that the compressor second stage inlet receives fluid from the interstage separation device outlet and a compressor second stage outlet in fluid communication with an inlet of the second stage cooling device so that the inlet of the second stage cooling device receives fluid from the compressor second stage outlet.

4. The system of claim 2 wherein the discharge separation device includes a liquid outlet and further comprising a junction, said junction configured to receive and combine discharge vapor from the discharge separation device vapor outlet and discharge liquid from the discharge separation device liquid outlet and said junction having a junction outlet in fluid communication with the primary refrigeration passage of the main heat exchanger.

5. The system of claim 2 wherein the discharge separation device includes a liquid outlet in fluid communication with the primary refrigeration passage of the main heat exchanger.

6. The system of claim 2 wherein the main heat exchanger includes a mixed refrigerant cooling passage configured to receive and condense mixed refrigerant from the vapor outlet of the discharge separation device and further comprising a first expansion device configured to receive and expand condensed mixed refrigerant from the mixed refrigerant cooling passage and to direct expanded mixed refrigerant to the primary refrigeration passage.

7. The system of claim 1 wherein the mixed refrigerant compression system includes a mixed refrigerant primarily made up of methane, ethylene and propane.

8. The system of claim 1 wherein the main heat exchanger includes a warm end that receives the effluent stream and a cold end from which the mixed phase effluent stream exits the main heat exchanger, the system further comprising a propane feed expansion device configured to receive and expand a feed stream containing propane that is independent of the effluent stream so that an expanded feed stream is produced, said main heat exchanger also configured to receive and warm the expanded feed stream in the warm end so as to provide cooling for the effluent stream.

9. The system of claim 1 wherein the main heat exchanger includes a warm end that receives the effluent stream and a cold end from which the mixed phase effluent stream exits the main heat exchanger, said main heat exchanger configured to receive and warm the combined stream in the warm end so as to provide cooling for the effluent stream.

10. The system of claim 1 wherein the separation system includes a single separation device.

11. The system of claim 1 wherein the junction is external to the main heat exchanger.

12. The system of claim 1 wherein the split is configured to receive and divide the separated vapor stream as a superheated vapor stream into a recycle gas stream and a net vapor stream, wherein both of the recycle gas stream and the net vapor stream are superheated hydrogen rich vapor streams.

13. The system of claim 1 wherein the split is configured to receive and divide the separated vapor stream into a recycle gas stream and a net vapor stream having matching hydrogen-rich compositions.

14. The system of claim 1 wherein the main heat exchanger is a single heat exchanger.

15. A method for separating olefinic hydrocarbon and hydrogen in an effluent fluid stream from a dehydrogenation reactor comprising the steps of:

a. partially condensing the effluent fluid stream so that a mixed phase effluent stream is formed;
b. separating the mixed phase effluent stream into a separated vapor stream containing hydrogen and a separated liquid stream containing an olefin product;
c. dividing the separated vapor stream as a single phase vapor stream into a recycle gas stream and a net vapor stream, wherein both of the recycle gas stream and the net vapor stream are single phase vapor streams;
d. combining at least a portion of the recycle gas stream with a propane stream that is independent of the effluent stream to form a combined stream;
e. warming the net vapor stream, the combined stream, the separated liquid stream and a refrigerant stream to provide refrigeration for partially condensing the effluent fluid stream.

16. The method of claim 15 wherein the refrigerant stream used in step e. includes a mixed refrigerant.

17. The method of claim 16 wherein the step of partially condensing the effluent fluid stream is accomplished using both the mixed refrigerant and a stream containing propane and a portion of the separated vapor stream.

18. The method of claim 16 wherein the mixed refrigerant is primarily made up of methane, ethylene and propane.

19. A system for separating an olefinic hydrocarbon and hydrogen in an effluent fluid stream from a dehydrogenation reactor comprising:

a. a main heat exchanger configured to receive and partially condense the effluent fluid stream so that a mixed phase effluent stream is formed;
b. a separation system configured to receive and separate the mixed phase effluent stream into a separated vapor stream including hydrogen and a separated liquid stream including an olefinic hydrocarbon;
c. a split configured to receive and divide the separated vapor stream as a single phase vapor stream into a recycle gas stream and a net vapor stream, wherein both of the recycle gas stream and the net vapor stream are single phase vapor streams;
d. a junction configured to receive and combine a propane stream, where the propane stream is independent of the effluent stream, and at least a portion of the recycle gas stream so that a combined stream is formed;
e. said main heat exchanger configured to receive and warm the net vapor stream, the combined stream and the separated liquid stream to provide refrigeration in the main heat exchanger;
f. a refrigerant compression system configured to provide refrigeration in the main heat exchanger.

20. The system of claim 19 wherein the separation system includes a single separation device.

* * * * *